United States Patent [19]

Sidey

[11] 4,453,401
[45] Jun. 12, 1984

[54] PRESSURE SENSOR AND SOIL STRESS ISOLATION FILTER ARRANGEMENT IN A PORE PRESSURE PROBE

[75] Inventor: Roger Sidey, Richmond, England

[73] Assignee: The United States of America as represented by the Secretary of the Air Force, Washington, D.C.

[21] Appl. No.: 357,439

[22] Filed: Mar. 12, 1982

[51] Int. Cl.³ .................. G01L 11/00; G01N 33/24
[52] U.S. Cl. ........................................ 73/73; 73/754
[58] Field of Search ................. 73/73, 300, 301, 754

[56] References Cited

U.S. PATENT DOCUMENTS

| | | | |
|---|---|---|---|
| 2,259,867 | 10/1941 | Webster | 73/300 |
| 2,459,268 | 1/1949 | Elkins | 73/300 |
| 3,031,591 | 4/1962 | Cary | 73/754 |
| 3,318,140 | 5/1967 | Shields et al. | 73/73 |
| 3,374,664 | 3/1968 | Lefelhocz et al. | 73/73 |
| 3,456,509 | 7/1969 | Thordarson | 72/406 |
| 4,332,172 | 6/1982 | Torstensson | 73/73 |
| 4,408,481 | 10/1983 | Sidey | 73/73 |

Primary Examiner—Charles Frankfort
Assistant Examiner—Denis E. Corr
Attorney, Agent, or Firm—Donald J. Singer; John R. Flanagan

[57] ABSTRACT

A system for measuring transient pore water pressure in the ground utilizes a probe member having a unique arrangement of a pressure sensor and a soil stress isolation filter. The probe member has a body portion with a hollow cavity defined therein. The pressure sensor in the form of a ceramic transducer is mounted in the cavity, and the filter in the form of a circumferential gap formed on the body communicates with the cavity. The filter is also configured for isolating the sensor from effective soil fabric stresses while allowing access to the transducer by pore water pressure. A coupling medium in the form of silicon grease fills the cavity so as to transmit the pore water pressure to the transducer.

5 Claims, 7 Drawing Figures

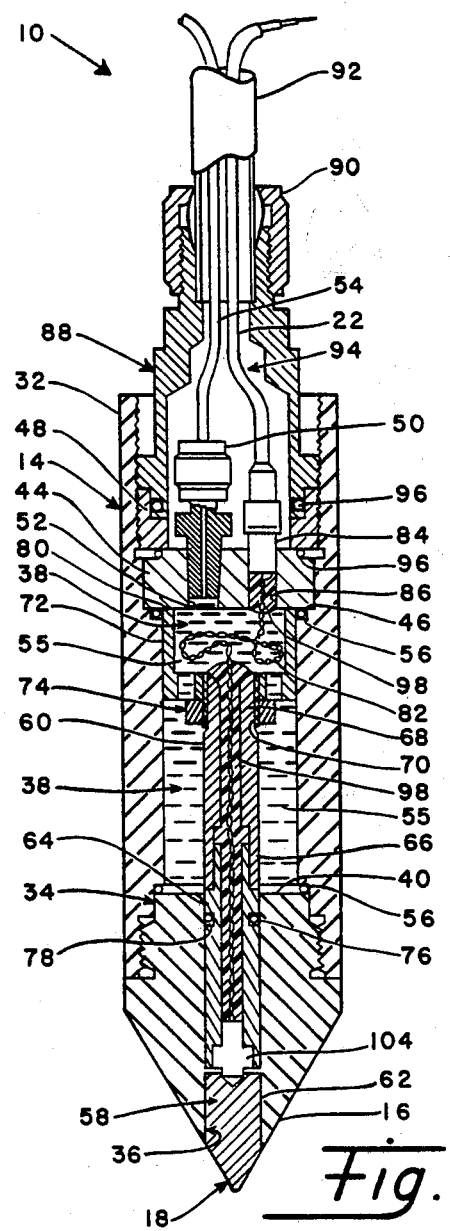
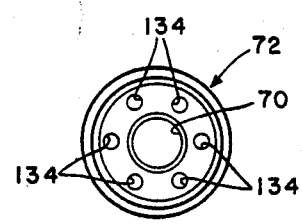
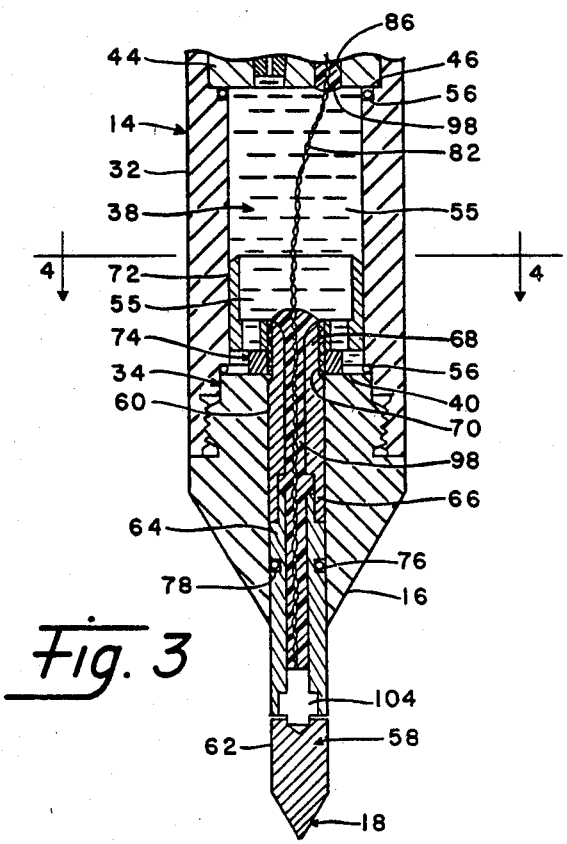
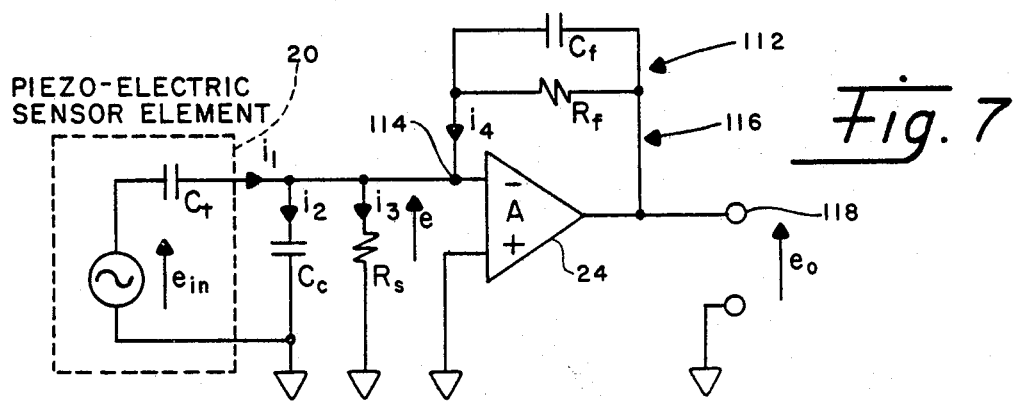

PRESSURE SENSOR AND SOIL STRESS ISOLATION FILTER ARRANGEMENT IN A PORE PRESSURE PROBE

RIGHTS OF THE GOVERNMENT

The invention described herein may be manufactured and used by or for the Government of the United States for all governmental purposes without the payment of any royalty.

CROSS REFERENCE TO RELATED APPLICATION

Reference is hereby made to the following co-pending U.S. application dealing with related subject matter and assigned to the assignee of the present invention: "Pore Pressure Probe Assembly and Two-Stage Emplacement Thereof" by Roger Sidey, U.S. Ser. No. 357,444, filed Mar. 12, 1982 now U.S. Pat. No. 4,408,481.

BACKGROUND OF THE INVENTION

1. Field of the Invention

The present invention broadly relates to the measurement of transient pore water pressure in soils and, more particularly, is concerned with a system for measuring dynamic pore pressure which utilizes a unique arrangement of a pressure sensor and a soil stress isolation filter in a probe member of the measuring system.

2. Description of the Prior Art

Despite significant advances in recent years toward understanding the behavior of soils under dynamic or shock loading conditions, relatively little is known of the way in which transient pore water pressures affect the response of saturate soils. Much effort has been devoted to the development and refinement of instrumentation for measurement of stresses and motions in soils subjected to loading; however, in contrast, there appears to be a marked absence of work in the area of transient pore water pressure measurement.

There are some difficult problems associated with measurement of the transient behavior of pore water pressure, particularly when the distrubance is blast induced. First, blast or shock generated pressure pulses require a significantly faster responding instrument than that required in conventional piezometer applications. Next, a large dynamic range of response is required since peak pressures at the start of the loading are typically very large compared to the pressures remaining behind the blast wave. Furthermore, peak amplitudes of blast induced pressures are often difficult to predict. Finally, placement of the probe is critical because soil distrubance due to the placement can significantly affect the measurement.

With respect to the last-mentioned problem, the distribution of dynamic pore pressure in a soil mass resulting from a disturbance or fluctuation is critically dependent upon local permeability. Disturbance or remoulding of the soil due to placement of instrumentation is therefore an important consideration. In a saturated soil the lumped effective bulk modulus (a critical factor affecting propagation velocity and attenuation of dynamic disturbances) is high. If, during placement, a piezometer introduces any voids of air, a massive local reduction of this parameter can be created. The effect of such a disturbance vanishes rapidly with increasing distance from the inclusion and invariably the total soil mass system will not realize the effect. However, the piezometer at the center of the disturbed zone will register an unrepresentative dynamic pressure history.

From the above-described problems associated with transient pore water pressure measurement, it would be reasonable to conclude that the ideal measurement device would be physically small as possible, equivalent to, or less than, the nominal grain size of the soil mass. Apart from the immediately apparent problems in the design and manufacture of such a device, it is difficult to imagine how it could be utilized for a practical in situ measurement. Furthermore, there would be the problem of isolating the pressure sensor from effective stresses in the soil fabric. For a device so small these loads would be imposed highly irregularly from the surrounding soil grains. Clearly some form of compromise must be struck between size and durability of the measurement device.

In view of the above-described problems associated with the measurement of transient behavior of pore water pressure, the need exists for a measurement device small in size and having a fast response time, but rugged enough to survive emplacement and subsequent operating conditions.

SUMMARY OF THE INVENTION

The preferred embodiment of a system for measuring dynamic pore water pressure, as disclosed herein, has several unique features which are designed to satisfy the aforementioned needs. Two features employed by the measuring system are a unique probe assembly and two-stage emplacement technique therefor. In the initial stage, the probe assembly in the system is emplaced by pushing it into the ground. Such step, used extensively in cone penetrometer site investigations, applies relatively high stresses to the probe assembly. However, the probe assembly includes a secondary probe member which contains a miniature pressure sensor and is itself contained within a larger, more robust, primary probe member. The larger primary member is used as a vehicle to protect the secondary probe member and the sensor and deliver them to the selected measurement region. At the desired depth of placement, in the final stage of the technique, the secondary probe member containing the sensor is ejected into the soil. The secondary member is pushed into the undisturbed soil ahead of the larger primary member. While the aforementioned features comprise the invention claimed in a co-pending application, cross-referenced above, its construction and function are illustrated and described herein for facilitating a complete and thorough understanding of the feature of the system comprising the present invention.

The present invention relates to another feature of the measuring system, such being a unique arrangement in a probe member of a miniature pressure sensor in the form of a fast response piezometer capable of a frequency response extending beyond 1 kHz in a cavity in the probe member, a soil stress isolation filter through which the sensor is capable of achieving a responsive coupling with the interstitial fluid in the region of measurement while being protected from loading by the fabric of the insitu soils, and a coupling medium in the cavity about the sensor for transmitting the pore water pressure to the sensor. The simplicity and inherent ruggedness of the measuring system allows its sensor to operate over a broad range of pressures encompassing those encountered in blast loading conditions. The particular form which the soil stress isolation filter takes provides the measuring system with a number of advantages. It is simple in construction and is inherently a more convenient and flexible arrangement in assemblying the probe member for operation.

More particularly, the filter is comprised by an annular slit aperture about the body of the probe member in the form of a narrow circumferential gap formed at a connection of first and second tip sections thereof, and a plurality of radial openings are formed through the body for communicating the gap with the cavity.

BRIEF DESCRIPTION OF THE DRAWINGS

FIG. 2 is an enlarged cross-sectional view of the probe assembly of the measuring system of FIG. 1, showing the secondary probe member in its retracted position within the tip of the primary probe member.

FIG. 3 is a fragmentary cross-sectional view similar to that of FIG. 2, but showing the secondary probe member in its extended position after ejection from the tip of the primary probe member.

FIG. 4 is a top plan view of the cable cup of the primary probe member as seen along line 4—4 of FIG. 3.

FIG. 7 is a simplified schematic diagram of the low frequency measurement circuit used in the measuring system of the present invention.

DETAILED DESCRIPTION OF THE INVENTION

In General

Figure 1:
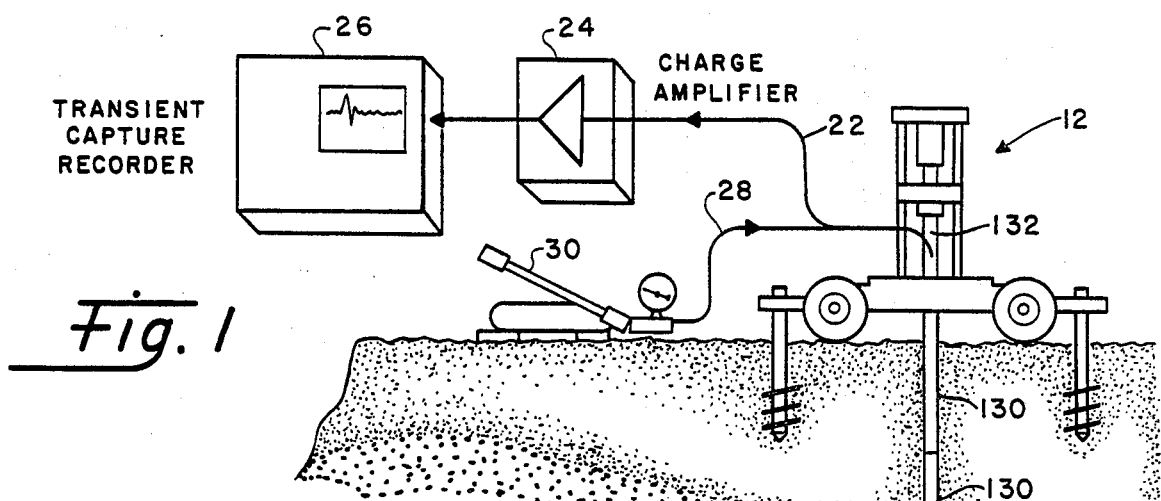
FIG. 1 is a schematic view of the system for measuring dynamic pore pressure of the present invention shown in conjunction with the apparatus for emplacement of the probe assembly of the measuring system into the ground.

Referring now to the drawings, and more particularly to FIG. 1, there is shown in schematical form the system for measuring dynamic pore water pressure which employs a probe assembly, generally designated 10, which utilizes the unique pressure sensor/soil stress isolation filter arrangement of the present invention. The system is shown in conjunction with apparatus for two-stage emplacement of the probe assembly 10 of the measuring system into the ground. In the exemplary embodiment in FIG. 1, the emplacement apparatus takes the form of a conventional penetrometer driving or pushing rig, generally designated 12.

As more clearly seen in FIGS. 2 and 3, the probe assembly 10 includes a large, robust primary probe member 14 which contains in its outer tip end 16 a small, secondary probe member 18 which, in turn, houses a miniature pressure sensor 20. Preferably, the sensor 20 is in the form of a piezoelectric ceramic pressure transducer which generates an electrical charge in response to pressure being applied thereto. Being highly stiff and possessing practically no damping, the transducer characteristics of the basic material are highly linear and the range of pressures over which a usable signal can be achieved is extremely broad. Laboratory testing has demonstrated that the sensor is capable of a frequency response extending beyond 1 kHz. The piezoelectric pressure transducer is self-generating, that is, the power in the output signal is derived from the mechanical input to the sensor 20. No electrical energization is required and, hence, the number of connections to the sensor is correspondingly minimal. Leadwire cable 22 connects the sensor to a charge amplifier 24 which, in turn, is connected to a recorder 26 for reproducing a graphical representation proportional to the stresses applied to the sensor 20 by surrounding pore water.

During emplacement of the probe assembly 10, the secondary probe member 18 is retained within the larger primary probe member 14 in a retracted position, as seen in FIG. 2. Once the desired depth of emplacement in the ground is reached, the secondary probe member 18 is ejected from the tip 16 of the primary probe member 14 to an extended position as seen in FIG. 3. Ejection of the secondary probe member occurs at a rate controlled by hydraulic fluid pumped through line 28 by operation of hand pump 30 in FIG. 1. The two-stage emplacement technique which has just been briefly described will be discussed in greater detail later on.

Pore Water Pressure Measuring System

As mentioned above, the probe assembly 10 is comprised by three basic parts: the primary probe member 14; the secondary probe member 18; and the pressure sensor 20.

As seen in FIGS. 2 and 3, the primary probe member 14 includes a hollow tubular probe case 32 and a major cone 34 threadably attached to the lower end of the probe case. Preferably, the major cone 34 is manufactured from tool steel material which has subsequently been through-hardened by heat treatment. The particular type of steel chosen (OHNS—oil quench hardening, nonshrinking) is specially formulated to maintain dimensional stability during the hardening process. The major cone 34 is solid except for a central bore 36 formed therein through which is slidably mounted the secondary probe member 18. The upper end of the probe case 32 is internally threaded for attaching the probe assembly to the penetrometer driving rig, as will be explained later.

A pressure chamber 38 is formed in the hollow probe case 32 between the inner flat end 40 of the major cone 34 and the lower side 42 of a bulkhead or cap 44 which is retained against an annular seating shoulder 46 in the probe case 32 by a retaining nut 48. The nut 48 is threaded externally for mating with the internal threads in the upper end of the probe case 32. The pressure chamber 38 communicates with the hand-operated pump 30 of FIG. 1 through a connector 50 threaded in an opening 52 in the bulkhead cap 44. The connector 50 anchors one end of an uphole hydraulic tube 54 of hydraulic line 28 in communication with the chamber 38. Hydraulic fluid 55, preferably in the form of silicone grease, is retained in the chamber 38 by static O-ring seals 56 located at opposite ends of the chamber, and seated on internal shoulders in the case 32, adjacent the inner flat end 40 of major cone 34 and the lower side 42 of cap 44, respectively.

The secondary probe member 18, as seen in FIGS. 2 and 3 and in more detail in FIG. 4, includes a lower cylindrical instrumented tip 58 and an upper cylindrical extension rod 60. The instrumented tip 58 has an outer tip section (or minor cone) 62 and an inner tip section 64 which at its inner end is threadably connected to a lower end 66 of the extension rod 60 whereby the instrumented tip 58 and extension rod 60 acts as a unitary member. An upper end 68 of the extension rod 60 is externally threaded for attachment in a threaded bore 70 in a cable cup 72. The cable cup 72 and extension rod 60 are prevented from unthreading from one another by lock nut 74 threaded on the upper end 68 of the extension rod 60 below the cable cup 72 and tightened thereagainst.

With the secondary probe member 18 in its retracted position as seen in FIG. 2, its extension rod 60 extends above the rear or inner flat end 40 of the major cone 34 into the pressure chamber 38. An O-ring seal 76 mounted within an annular groove 78 on the inner tip section 64 of the instrumented tip 58 adjacent the lower end 66 of the extension rod 60 maintains an effective seal between the major cone 34 and the instrumented tip 58 during its movement from the retracted (FIG. 2) to extended (FIG. 3) positions.

In order to retain the instrumented tip 58 in the fully retracted position of FIG. 2, a low strength bonded joint is made at 80 between the upper rim of the cable cup 72 and the bottom surface of the bulkhead cap 44. The bonding agent chosen is a cyanoacrylate thin film adhesive (Loctite IS495), and the quantity used is just sufficient to achieve a joint with a reasonable strength. The purpose for bonding these two components together is convenience in assembling the probe assembly components together, retaining the secondary probe member 18 in its fully retracted position during moving or handling of the probe assembly 10, and protecting the extra coiled lengths of insulated copper wires 82. These wires of the leadwire cable 22 interconnect the sensor 20 through the hollow center of the instrumented tip 58 and extension rod 60 with a cable plug 84 threaded in another opening 86 in the bulkhead cap 44.

A connector cover 88 is threaded within the upper end of the probe case 32 and has an adapter compression fitting 90 threaded on its upper end for grasping the end of the nylon tubular sheath 92 which houses the electrical cable 22 and hydraulic tube 54 and provides a watertight housing for the uphole connection system. When the connector cover 88 is tightened to a home position against the retaining nut 48, the connector cover and nylon tubular sheath form a hermetically sealed chamber 94 for the electrical and hydraulic connections to the probe assembly 10. Another pair of O-ring seals 96 assist in hermetically sealing access to the chamber 94 from the pressure chamber 38 and the exterior of the case 32.

Figure 5:
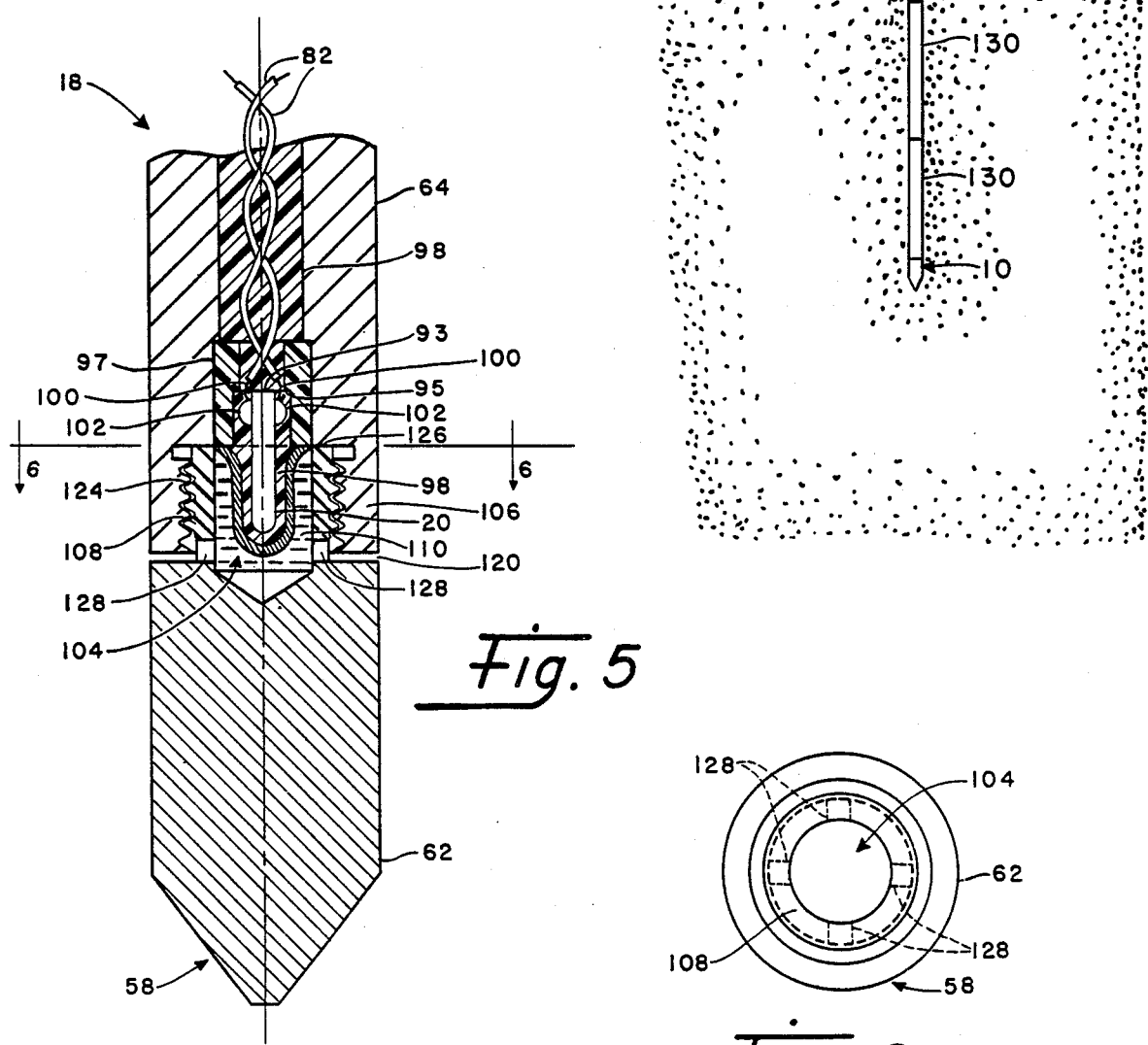
FIG. 5 is an enlarged fragmentary cross-sectional view of the secondary probe member of the probe assembly of FIG. 2.

The heart of the probe assembly 10 comprising the present invention is illustrated in detail in FIG. 5. It is the arrangement of the miniature pressure sensor 20 and the structures of the respective body portions of the outer and inner instrumented tip sections 62,64 of the secondary probe member 18. The structures define a cavity which surrounds and houses the pressure sensor 20 and forms a filter which isolates the sensor from effective soil fabric stresses while allowing access to it by pore water pressure. As mentioned earlier, the pressure sensor 20 preferably takes the form of a piezoelectric ceramic pressure transducer. More particularly, the transducer preferably has a rectangular plate-like or slither configuration with a base 93 mounted against a shoulder 95 of a bushing 97. The bushing 97 and the transducer are potted using epoxy resin 98 into the inner instrumented tip section 64 of the secondary probe member 18. The epoxy resin potting 98 extends up the length of the hollow center of the extension rod 60 and is also applied below cable plug 84. Bare copper wires 100 are attached by soldered connections 102 to the bulkhead end of the sensor 20 and approximately the lower half of the sensor protrudes into pressure sensor cavity 104 formed at the threaded connection between the lower end 106 of the hollow inner tip section 64 and the hollow upper end 108 of the outer tip section 62 of the secondary probe member 18. This lower protruding half of the sensor 20 is protected by a dip coating of epoxy resin potting 98 and a coating of parafin wax 99 to provide an impervious moisture barrier. It is this part of the sensor 20 which is used to sense pressure in a coupling medium 110 to be described shortly. The relatively thin coat of epoxy resin, together with the extremely high stiffness of the ceramic transducer material, result in minimal attenuation of the pressure applied to the transducer from the coupling medium 110. In the applications for which the probe assembly 10 is designed, i.e., blast induced pore pressure variations, the design maximum pressure is high. The corresponding signals from the sensor 20 are of high amplitude compared to the inherent electrical noise in the measurement system and can, therefore, tolerate a considerable amount of attenuation before the performance of the system is degraded.

In order to act as an energy conversion device, the transducer must possess a polarization or intrinsic orientation. This process is carried out at the manufacturing state and results in the transducer possessing a sensitive direction or axis, along which the stresses that are required to be measured must act. The transducer 20 is a relatively thin plate with a length of 6 mm, with a width of 2 mm and thickness of 1 mm. Its direction of polarization is normal to the larger, opposite 6×2 mm surfaces. This configuration minimizes the de-sensitizing effect or attenuation due to Poisson's ratio of the material, and provides the additional benefit of maximizing the electrical capacitance of the transducer.

The piezoelectric transducer as used in the measuring system may be modelled as a voltage generator in series with a capacitor. The output of the voltage generator is proportional to the stress applied to the transducer and the capacitance is the physical value measured at the connections to the device by the electrical circuit 112, schematically shown in FIG. 7, which includes operational amplifier 24 set up as a high gain differential type. In the arrangement of FIG. 7, the voltage generator or transducer 20 feeds directly into the summing junction 114 of the differential amplifier 24. With the amplifier connected in the inverting mode, the summing junction 114 appears virtually as a short circuit across the voltage generator or source, the transducer or sensor 20. The effect of the amplifier is to balance the flow of current into the junction 114 from the voltage generator (the transducer), with an opposing current derived via a feedback network, generally designated 116, from the output 118 of the circuit 112. Under these conditions it is the input charge (i.e., product of total effective source or transducer capacitance and the open circuit output voltage of the source or transducers) which is balanced. The amplifier balances the currents at the summing junction 114 by developing a charge across the feedback capacitor $C_f$ which opposes the input charge. In this way the output voltage of the amplifier 24 reproduces the input charge signal from the source or transducer 24.

Mention was made previously of a pressure coupling medium 110, such being preferably silicone grease. The coupling medium 110 is used to fill the spaces in the pressure sensor cavity 104 and the aforementioned soil stress isolation filter, generally designated 120, and transmit pore water pressure to the pressure sensor 24. The coupling medium 110, to be effective, must be fluid, or at least, have negligible shear strength and, in order to achieve a fast response for the system, it must be relatively incompressible. Silicone grease was found to meet these requirements. While not a true fluid in the sense that the grease can maintain a certain amount of physical form, it possesses only a minimal shear strength. The particular benefits afforded by the silicone grease are due to its excellent water imperviousness and insulation resistance characteristics, and to the fact that it does not seem to noticeably degrade the high frequency response of the probe assembly.

Figure 6:
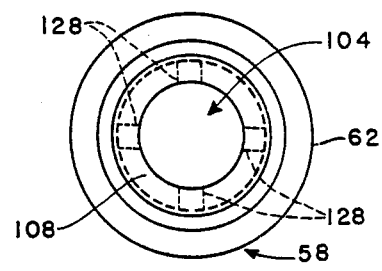
FIG. 6 is a top plan view of the upper end of the outer instrumented tip section of the secondary probe member as seen along line 6—6 of FIG. 5.

The function of the above-mentioned soil stress isolation filter 120 is to provide an effective stress isolation barrier which will allow pore water pressure to be transmitted via the coupling medium to the transducer cavity 104, but prevents loading of the transducer by the fabric of the in situ soils. The filter 120 takes the form of an annular slit aperture 122 formed when the lower end 106 of the inner tip section 64 and the upper end 108 of the outer tip section 62 are tightened together. From the outside the aperture 122 appears as a narrow circumferential gap about the circumference of the secondary probe member 18 at the joint where its upper and lower tip sections are assembled together. The dimension of gap is controlled by the bottoming-out action of a threaded shoulder 124 of the upper end 108 of the outer tip section 62 on a flat annular inner surface 126 of the lower end 106 of the inner tip section 64. The dimension of the gap can be adjusted by placing shim washers between the shoulder 124 and inner surface 126. As will be explained in detail later, stresses due to emplacement of the probe assembly 10 are transmitted through this shoulder 124, and the coupling medium 110 acts through a number of radial holes 128 (see FIGS. 5 and 6) through the shoulder 124 adjacent the top of the solid minor cone portion of the outer instrumented tip section 62. Laboratory testing of the aperture filter showed that it introduced no discernible effect on the frequency response of the probe assembly 10 even at gap widths down to 0.2 mm. It was felt that, at this dimension, the likelihood of a soil fabric penetrating the filter and stressing the pressure sensor 20 was extremely small, particularly bearing in mind the viscous nature of the silicone grease coupling medium 110. Also, this configuration for the stress isolation filter 120 reduces problems with de-airing the assembly 10 by allowing it to be de-aired in the dismantled state where all recesses and surfaces of the sensor cavity 104 and the stress filter 120 are readily accessible. Hence, the surfaces forming the filter 120, and all regions of the interior of the pressure sensor cavity 104, can be thoroughly and conveniently wetted with the coupling medium 110 prior to assembly.

The use of silicone grease as the pressure coupling medium 110 has provided an additional practical benefit. Being adjusted by the use of suitable additives, the viscosity of the substance can be arranged to remain virtually constant over a wide range of temperatures. The particular grease chosen for the pressure coupling medium 110, silicone grease, is a commonly available type, such as General Electric G-623 or equivalent, designed for electrical insulation and moisture proofing applications. It is relatively viscous and has the property that it will not run off; even over prolonged periods the substance retains form. This property of the medium has been exploited to eliminate the need to seal the pressure sensor cavity 104. The instrumented tip 58 is packed with grease or coupling medium 110 by injecting it into its outer and inner tip sections 62, 64. Upon screwing the tip sections together, the excess grease is extruded out through radial holes 128, permeating the voids and filling the circumferential slit filter aperture 122. The outside of the instrumented tip 58 of the secondary probe member 18, located as a free fit in the major cone 34 of the primary probe member 14, is surrounded by a silicone grease film. The static properties of the grease are relied upon to retain the grease within the probe assembly 10. The grease as mentioned earlier also serves as the ejection hydraulic fluid or medium 55 for ejection of the secondary probe member 18 through use of the two-stage emplacement technique of the present invention to be described below. Once the probe assembly is emplaced in the saturated soils with the instrumented tip 58 ejected from the major cone, the interface between the local pore water and the silicone grease coupling medium occurs at the outside edge of the annular slit aperture 122, the external grease film on the instrument tip being wiped off by the surrounding soils.

TWO-STAGE EMPLACEMENT TECHNIQUE

As mentioned initially, a two-stage technique is utilized for emplacement of the probe assembly 10. In the preferred embodiment, the probe assembly 10 is emplaced in the ground by means of a conventional penetrometer pushing rig 12 utilizing a system of stout hollow rods 130. Being susceptible to buckling under driving loads, the rods 130 are relatively short and arrange in a string, as seen in FIG. 1, being connected one to the next by threaded joints at each end. The sheath 92 which houses the electrical and hydraulic connections to the probe assembly is accommodated within the hollow center of the rod string and leads out of the string at a slot (not shown) on the driving cap 132 of the string to the hand operated pump 30.

A major portion of the loading applied to the probe assembly 10 during emplacement by the penetrometer pushing rig 12 arises from end stress. This stress, brought about by the displacement and remoulding of the soil into which the probe assembly 10 is pushed, acts across the forward projected area of the assembly 10 and combines with wall friction forces to produce a net push-down load. The order of the push-down load to be expected is determined by the type of soil and the relative density of the soil deposit.

During the initial phase or stage of emplacement of the probe assembly 10, the second probe member 18 (and thereby its instrumented tip 58) is contained within the larger, protective, primary probe member 14. The major cone 34 of the primary probe member 14 prevents the instrumented tip 58 of the secondary probe member 18 from coming into any substantial or significant contact with the unsaturated soils, and absorbs the bulk of the loading and wear involving in reaching the desired measurement region depth. In order to avoid entraining air in the probe assembly 10 and thus subsequently introducing it into the saturated soils in the measurement region, the exterior of the probe assembly 10 is designed with a minimum of surface features. By using the simply shaped pointed cylinder configuration for both the primary and secondary probe members 14, 18, there is least risk of trapping air. Furthermore, for the secondary probe member 18, the configuration conveniently allows saturation of the clearance space in the central bore 36 of the major cone 34 of the primary probe member 14 due to the pressure of the silicone grease coupling medium 110.

The configuration does, however, potentially possess the drawback that the stresses acting over the tip end of the secondary probe member 18 cannot be coupled into the major cone 34 of the primary probe member 14. Without some form of step or shoulder on the secondary probe member 18, acting onto a corresponding feature on the major cone 34, the tip stresses cannot be transferred to the cone 34 and so must be carried from within the probe assembly 10. That is exactly what is achieved by the structure of the secondary probe member 18.

The end load developed at the tip of the outer tip section 62 is transmitted past the pressure measurement area of the secondary probe member 18, being located approximately in the region of the cavity 104 and sensor 20, to the inner tip section 64 by the threaded coupling formed by the upper and lower ends 108, 106 of the respective tip sections 62, 64. As described earlier, this coupling is used to implement the effective stress filter 120 for the measurement system by being arranged to bottom out so as to produce the circumferential slit aperture 122. Driving loads against the secondary probe member tip are thus transmitted through this coupling feature by the threaded shoulder 124 of the outer tip section 62 where it seats in a recess or annular surface 126 in the inner tip section 64.

Above the major cone within the probe assembly, another threaded joint or coupling between the inner tip section 64 and the extension rod 60 couples the load into the extension rod. The rod 60 terminates in a threaded connection with the cable cup 72 which, in turn, is bottomed at its upper rim against the rear bulkhead cap 44 of the ejection pressure chamber 38. As mentioned previously, the cap 44 is retained against a seating shoulder 46 in the probe case 32 by retaining nut 48. It is, therefore, by way of the bulkhead cap 44 and retaining nut 48 that the secondary probe member tip loads finally enter the probe case 32 to merge with those arising from the major cone 34 of the primary probe member 14. The net push-down force for the probe assembly due to end load and wall friction is applied from the hollow driving rods 130 to the upper end of the probe case 32 to which the lower one of the rods 130 is threadably attached.

Having reached the desired measurement location the initial emplacement stage ends and the procedure of the second stage is brought into action, that is, the secondary probe member 18 is ejected from the outer tip end 16 of the primary probe member 14. This is achieved by manually actuating the hand pump 30 so as to pressurize via hydraulic tube 54 of hydraulic line 28 the ejection pressure chamber 38 within the probe case 32 between bulkhead cap 44 and the inner end 40 of the major cone 34. The chamber 38 is packed with a hydraulic medium 55 in the form of silicone grease 55 and the secondary probe member 18 becomes displaced relative to the primary probe member 14 when more hydraulic fluid is pumped into the chamber.

It will be recalled that the rim of the cable cup 72 and the pressure chamber bulkhead cap 44 are bonded together at 80 in order to retain the secondary probe member 18 in its fully retracted position (FIG. 2). However, it will be recalled further that the bond 80 is just sufficient to achieve a joint with a resonable strength. To eject the probe member 18, this bond 80 must be broken. By bringing the pressure in the chamber 38 up to a pressure of 1000 to 1500 lb. per square inch, the bond 80 will break between the cable cup 72 and the cap 44. Due to the position displacement characteristic of the hydraulic system and the damping action of the silicone grease packing 55, only a slight jump or step movement of the secondary probe member 18 occurs. Thereafter the secondary probe member is ejected to its position of FIG. 3 at a rate controlled by the volumetric displacement of the hand pump 30 being used. Travel of the probe member 18 is stopped by the bottoming action of the cable cup lock nut 74 on the inner flat end 40 of the major cone 34. The series of holes 134 through the cable cup 72 (FIGS. 2-4) allows the cup to move through the pressurized grease-filled chamber. The insulated electrical wires 82 within the chamber 38 are adapted to withstand the ejection chamber pressure, as are its interconnections with the extension rod 60 and the cable plug 84 which are filled with epoxy resin potting 98.

It will be understood that the secondary probe member 18 is retrieved along with the rest of the probe assembly 10 when the latter is pulled from the ground by reverse operation of the rig 12. However, a design could readily be produced in which the secondary probe is fully ejected from the primary probe member 14. Here, the primary probe member would be withdrawn, leaving behind the miniature sensor and the secondary probe member from which signals could continue to be retrieved through suitable cable.

In the amplifier feedback circuit of FIG. 7 and its relationship to the sensor 20 and cable parameters, the symbols have the following definitions and/or exemplary values:

$e_{in}$ = open circuit emf generated by the piezoelectric transducer or sensor 20, $q_{in}$ = charge generated by the transducer, $q_{in} = e_{in} \cdot C_t$, $e_o$ = output voltage of the amplifier 24, e = differential input voltage of the amplifier, $i_1$, $i_2$, $i_3$ and $i_4$ = summing junction currents, A = typically $10^5$, the low frequency differential voltage gain of the amplifier 24, $C_t$ = typically $2.2 \times 10^{-10}$F, the capacitance of the piezoelectric transducer 20, $C_c$ = 100 pF/m assuming 20 m of cable giving capacitance equal to $2 \times 10^{-9}$F, the capacitance of the connecting cable 82, $R_s$ = between $10^9$ and $10^{11}$ ohms, the shunt or leakage resistance across the transducer, $R_f$ = typically $10^9$ ohms (gives charge amplifier time constant of 0.5 sec.), the DC stabilization feedback resistance, and $C_f$ = typically $5 \times 10^{-10}$F, the Gain-determining feedback capacitor.

It is thought that the pressure sensor/soil stress isolation filter arrangement of the present invention and many of the attendant advantages thereof will be understood from the foregoing description and it will be apparent that various changes may be made in the parts thereof without departing from the spirit and scope of the invention or sacrificing all of its material advantages, the form hereinbefore described being merely a preferred or exemplary embodiment thereof.

Having thus described the invention, what is claimed is:

1. In a system for measuring transient pore water pressure in the ground, a probe member comprising:
    (a) a body portion having a hollow cavity defined therein and including an inner tip section and an outer tip section, said inner tip section having a lower hollow end, said outer tip section having an upper hollow end and adapted to be connected to said inner tip section at its lower hollow end such that said hollow cavity is formed between said inner and outer tip sections at the connection of said sections to one another;
    (b) a pressure sensor mounted in said cavity;
    (c) said inner and outer tip sections of said body portion having adjacent generally planar parallel spaced surfaces which define a filter in the form of a narrow circumferential gap disposed on said body portion at said connection of said inner and outer tip sections and open to the exterior of said body portion circumferentially thereabout, said circumferential gap defined between said parallel spaced surfaces of said inner and outer tip sections of said body portion being formed by bottoming-out of a recessed shoulder of said upper hollow end of said outer tip section on a flat annular inner surface of said lower hollow end of said inner tip section, said outer tip section further having a plurality of radially-extending holes defined therein in alignment with said circumferential gap and open to both said gap and said cavity for providing communication of pore water located about the exterior of said body portion with said cavity therein via said circumferential gap and said radially-extending holes while isolating said cavity and said sensor mounted therein from effective soil fabric stresses; and
    (d) a coupling medium disposed in said cavity between said sensor and said filter for transmitting pressure produced by said pore water to said sensor.

2. The probe member as recited in claim 1, wherein said plurality of radially-extending holes are defined through said recessed shoulder of said upper hollow end of said outer tip section in alignment with said circumferential gap.

3. The probe member as recited in claim 1, wherein said pressure sensor is a piezoelectric ceramic pressure transducer having a rectangular plate-like configuration.

4. The probe member as recited in claim 3, wherein said transducer is protected by a coating of epoxy resin potting and a coating of parafin wax to provide an impervious moisture barrier.

5. The probe member as recited in claim 1, wherein said coupling medium is silicone grease.

* * * * *